United States Patent [19]

Powell et al.

[11] 4,254,273

[45] Mar. 3, 1981

[54] PROCESS FOR PREPARING ESTERS OF α-METHYL-3,4-DIHYDROXYPHENYLALA-NINE

[75] Inventors: Burwell F. Powell, Neshanic, N.J.; Ralph F. Hirschmann, Blue Bell, Pa.

[73] Assignee: Merck & Co., Inc., Rahway, N.J.

[21] Appl. No.: 64,316

[22] Filed: Aug. 6, 1979

Related U.S. Application Data

[60] Continuation of Ser. No. 894,451, Apr. 7, 1978, abandoned, which is a continuation of Ser. No. 746,227, Dec. 1, 1976, abandoned, which is a division of Ser. No. 586,007, Jun. 11, 1975, abandoned.

[51] Int. Cl.$^3$ .................................... C07C 125/065
[52] U.S. Cl. .................................... 560/29; 260/326.4; 260/326.43; 260/340.5 R; 546/347; 560/40
[58] Field of Search .................................... 560/29

[56] References Cited

U.S. PATENT DOCUMENTS

| | | | |
|---|---|---|---|
| 3,829,456 | 8/1974 | Berman | 260/463 |
| 3,839,395 | 10/1974 | Otsuka et al. | 260/112.5 R |
| 3,852,338 | 12/1974 | Kaiser et al. | 260/501.12 |
| 3,859,331 | 1/1975 | Kaiser et al. | 260/463 |
| 3,891,696 | 6/1975 | Bodor et al. | 560/142 |
| 3,932,375 | 1/1975 | Nagasawa et al. | 560/29 |
| 4,007,173 | 2/1977 | Hoover et al. | 260/243 C |

FOREIGN PATENT DOCUMENTS

| | | |
|---|---|---|
| 45-19685 | of 1970 Japan | 560/29 |
| 45-36729 | of 1970 Japan | 560/29 |

OTHER PUBLICATIONS

Krail et al., Chem. Absts., 80, 83582(s), 1974.
Klieger, Liebigs Ann., 724, 204 (1969).
Broadbent et al., J. Chem. Soc., 2632 (1967).

*Primary Examiner*—Natalie Trousof
*Assistant Examiner*—G. T. Breitenstein
*Attorney, Agent, or Firm*—Salvatore C. Mitri; Daniel T. Szura

[57] ABSTRACT

Improved process for preparing esters of α-methyl-3,4-dihydroxyphenylalanine having pharmaceutical activity via novel N-(tert-butoxycarbonyl) intermediates.

3 Claims, No Drawings

PROCESS FOR PREPARING ESTERS OF α-METHYL-3,4-DIHYDROXYPHENYLALANINE

This is a continuation of application Ser. No. 894,451, filed Apr. 7, 1978, now abandoned, which in turn is a continuation of application Ser. No. 746,227 filed Dec. 1, 1976 now abandoned, which in turn is a division of U.S. application Ser. No. 586,007, filed June 11, 1975, now abandoned.

BACKGROUND OF THE INVENTION

Certain esters of DL- or L-α-methyl-3,4-di-hydroxyphenylalanine are effective in the treatment of hypertension. The compounds are generally administered in amounts of from about 0.005 to about 300 mg./kg. of body weight of the animal, preferably from about 0.05 to about 100 mg./kg., and especially from about 0.1 to about 25 mg./kg. of body weight of the animal. In this regard, it should be noted that the dosage should be adjusted depending upon the activity of the compound, the response desired in the reduction of blood pressure and also the weight of the animal. For the ranges given above, the more active compounds would tend to be given at the lower dosages and the less active compounds at the higher dosages.

In the preparation of esters of L-α-methyl-3,4-dihydroxyphenylalanine (also known as L-α-methyldopa or methyldopa), it is desirable to protect the amino group prior to esterification, otherwise the amino group may participate in the reaction and form undesired products.

It is kown that tert-butoxycarbonyl is an amino blocking group which is easily removed under mild conditions. Typically, the tert-butoxycarbonyl group may be removed by treatment with an acidic reagent such as gaseous hydrogen chloride or trifluoroacetic acid at ambient temperatures in solvents such as benzene or ethyl acetate. Attempts to prepare the N-tert butoxycarbonyl derivative of α-methyldopa via commonly used reagents such as tert-butoxycarbonyl azide were unsuccessful. It is an object of this invention to provide improved processes for preparing esters of α-methyl-3,4-dihydroxyphenylalanine having pharmaceutical activity via novel N-(tert-butoxycarbonyl)-intermediates.

Another object of this invention is the production of novel N-(tert-butoxycarbonyl)-intermediates which may be used in the preparation of pharmaceutically active esters of α-methyl-3,4-dihydroxyphenylalanine.

DETAILS OF THE INVENTION

It has been found that compound of the formula:

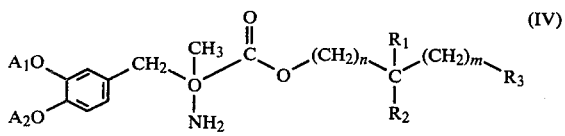

or a pharmaceutically acceptable acid addition salt thereof, wherein $A_1$ and $A_2$ are individually hydrogen or $C_{1-5}$alkanoyl,
$R_1$ and $R_2$ are individually hydrogen or $C_{1-5}$alkyl;
$R_3$ is selected from the group consisting of
 (A) a monocyclic or bicyclic heterocyclic radical containing from 3 to 12 nuclear carbon atoms and 1 or 2 nuclear hetero atoms selected from N and S with at least one being N, and with each ring in the said heterocyclic radical containing 5 to 6 members; and
 (B) the radical X—R$_4$
 wherein X is —O'—, —S—, or —NH— and R$_4$ contains up to 21 carbon atoms and is (1) a hydrocarbon radical or (2) an acyl radical of an organic acyclic or monocyclic carboxylic acid containing not more than 1 hetero atom in the ring; and
n and m are individually 0, 1, 2, or 3, may be prepared by removing the protective groups from a compound of formula III (see flow sheet).

More preferredly, the final amino ester products are those of formula IV wherein
$A_1$ and $A_2$ are hydrogen;
$R_1$ and $R_2$ are individually H or methyl;
$R_3$ is
 (A) the heterocyclic ring

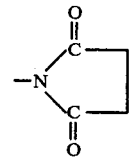

which may be substituted by $C_{1-3}$alkyl, or
 (B) the radical X-R$_4$
 wherein X is —O— or —NH— and R$_4$ is $C_{2-5}$alkanoyl; and
the n and m are 0, and especially α-succinimidoethyl α-methyl-3,4-dihydroxyphenylalaninate and α-pivaloyloxyethyl α-methyl-3,4-dihydroxyphenylalaninate.

The pharmaceutically acceptable acid addition salts may be prepared from the following acids which form acid addition salts with free base: hydrohalic acids such as hydrochloric, hydrobromic, perchloric, nitric or thiocyanic, a sulfuric or phosphoric acid or an organic acid such as formic, acetic, propionic, glycollic, lactic, pyruvic, oxalic, malonic, succinic, maleic, fumaric, malic, tartaric, citric, ascorbic, hydroxymaleic, dihydroxymaleic, benzoic, phenylacetic, 4-aminobenzoic, 4-hydroxybenzoic, anthranilic, cinnamic, mandelic, salicylic, 4-aminosalicylic, 2-phenoxybenzoic, 2-acetoxybenzoic, methanesulfonic, ethanesulfonic, hydroxyethanesulfonic, benzenesulfonic, p-toluenesulfonic, naphthalenesulfonic, sulfanilic, methionine, tryptophan, lysine or arginine-salts may be mono or polysalts.

Another aspect of this invention is esterifying compounds of formula II followed by removing the protective groups as outlined in the flow sheet, wherein
$R_5$ and $R_6$ are hydrogen, $C_{1-5}$alkanoyl or other suitable protective groups either individually or when taken together; and
Y is hydrogen, $[NR'_3H]^+$ wherein R' is $C_{1-5}$alkyl, pyridinium, substituted pyridinium, alkali metal or ½ (alkaline earth) metal.

Still another aspect of this invention is protecting the amino nitrogen of compounds of formula I, followed by esterifying the protected compound and removing the protective groups as outlined in the flow sheet.

Compounds of Formula II and III are novel compounds and a further aspect of this invention, especially those compounds of formula II wherein $R_5$, $R_6$ and Y are hydrogen and those compounds of formula III wherein $R_1$ and $R_2$ are individually hydrogen or methyl, $R_3$ is the heterocyclic ring

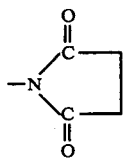

which may be substituted by $C_{1-3}$alkyl or $R_3$ is $-XR_4$ wherein X is $-O-$ or $-NH-$ and $R_4$ is $C_{2-5}$alkanoyl, n and m are 0, and $R_5$ and $R_6$ are hydrogen.

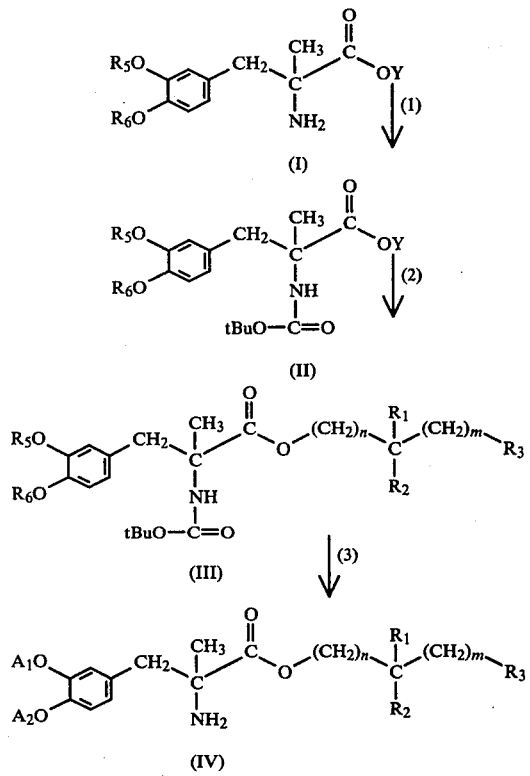

EQUIVALENTS

As those previously mentioned, including the appropriate restrictions.

REACTIONS AND CONDITIONS

The hydroxyl groups of α-methyldopa may be protected by reacting L-α-methyldopa (or the racemic mixture or derivatives thereof) with about 1.5 to 3.0 molar equivalents of dihalodiphenylmethane, di(halo)-di(substituted phenyl)methane or di(halo)di($C_{1-5}$alkyl) methane or 3.0 to 6.0 molar equivalents of pentafluorophenyl or 2,4,5-trichlorophenyl t-butoxycarbonyl, $C_{1-5}$alkanoyl halide, benzoyl halide, or substituted benzoylhalide, benzyl halide or substituted-benzyl halide. The preferred protective groups are the diphenyl-ketal or the acetyl esters. The reaction is normally carried out neat, with the excess O-blocking group reagent serving as the solvent, although an organic solvent such as those of step 1, may be present. The reaction may be carried out at a temperature of from about 100° C. to 230° C., preferably from about 180° C. to 200° C. until the reaction is substantially complete. Pressure is not critical and generally the reaction is carried out at atmospheric pressure in an open system.

The N-group of α-methyl-3,4-dihydroxyphenylalanine is protected by reacting L-α-methyl-3,4-dihydroxyphenylalanine (or the racemic mixture derivatives thereof) with about 1.0 to 5.0 molar equivalents of t-butyl 2,4,5-trichlorophenylcarbonate or t-butyl pentafluorophenylcarbonate (preferably 1.0 to 1.5 molar equivalents), neat or in a solvent (step 1). The reaction is carried out in the presence of a mild base (1.0 to 1.5 moles of base per mole of t-butylcarbonate reagent) which acts as an acid acceptor. The preferred starting material is L-α-methyl-3,4-dihydroxyphenylalanine. Solvents which may be used are amides (especially hexa$C_{1-5}$alkyl phosphoramides and di$C_{1-4}$alkyl alkylamides), nitriles (especially $C_{2-4}$alkylnitriles), heterocycles (especially pyridines and pyrrolidines), sulfoxides (especially di-$C_{1-5}$alkyl sulfoxide, sulfolane, and mixtures thereof. Examples of suitable solvents are dimethylformamide, dimthylacetamide, acetonitrile, pyridine, pyrrolidine, dimethylsulfoxide, sulfolane (tetrahydrothiophene-1,1-dioxide) and hexamethylphosphoramide. Preferred solvents are dimethylformamide (DMF), dimethylsulfoxide (DMSO) dimethylacetamide (DMA) and hexamethylphosphoramide (HMPA). Mild bases which may be used are alkali metal carbonates, alkaline earth carbonates, alkali metal bicarbonates, alkaline earth bicarbonates, pyridine, substituted pyridines and tertiary amines or mixtures thereof. Examples of suitable bases are pyridine (which may also act as the solvent), N($C_{1-5}$alkyl)-morpholines and tri($C_{1-5}$alkyl) amines such as diethylisopropylamine and triethylamine. The preferred base is triethylamine. The reaction may be carried out at a temperature from about 0° C. to the reflux temperature of the solvent, preferably from about 10° C. to 30° C. until the reaction is substantially complete. Pressure is not critical and generally the reaction is carried out at atmospheric pressure preferably in an inert atmosphere. The inert atmosphere may be gaseous nitrogen, carbon dioxide, helium, neon, argon or krypton or mixtures thereof, preferably nitrogen, argon or carbon dioxide.

The esterification (step 2) is carried out, using methods well known in the art such as by reacting L-(N-tert-butoxycarbonyl)-α-methyl-3,4-dihydroxyphenylalanine compound obtained from Step 1, supra, with about 0.8 to 1.2 molar equivalents of a compound of the formula:

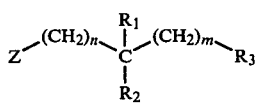

wherein

Z is chloro, bromo, iodo, or substituted $-SO_3$-group; and $R_1$, $R_2$, $R_3$, n and m are as defined above. The reaction may be carried out neat or in a solvent. Solvents which may be used are those of Step 1. The reaction is carried out in the presence of 1.0 to 1.5 moles of a mild base per mole of carboxylic acid which acts as an acceptor. Mild bases which may be used are those of Step 1. The reaction may be carried out at a temperature of from about 30° C. to the reflux temperature of the solvent, preferably from about 80° C. to 100° C. until the reaction is substantially complete. Pressure is not critical and generally the reaction is carried out at atmospheric pressure, preferably in an inert atmosphere. The inert atmospheres which may be used are those of Step 1. If desired, Step 2 may be carried out by merely adding the esterifying agent to the reaction mixture from Step 1.

Removal of the tert-butoxycarbonyl group (Step 3) from the product ester is accomplished by treating the carbonate in a solvent with 2 to 10 molar equivalents of a strong acid (pKa less than 3) per mole of protected ester. The solvents which may be used are water, $C_{1-5}$alkyl $C_{1-5}$alkanoates, $C_{1-5}$alkanoic acids, cyclo$C_{4-6}$alkyl ethers, halo$C_{1-5}$alkanes, $C_{1-5}$alkanols, halo$C_{1-5}$alkanoic acids and $C_{5-8}$aromatic hydrocarbons, or mixtures thereof such as ethyl acetate, formic acid, acetic acid, tetrahydrofuran (THF), chloroform, ethanol and benzene. The strong acids which may be used are those organic and inorganic acids having a pKa less than 3 such as Lewis acids, mineral acids and perhalo$C_{1-3}$alkanoic acids. Examples of suitable acids are boron trifluoride.etherate, aluminum trichloride, aluminum tribromide, methane sulfonic acid, para-toluene sulfonic acid, hydrochloric acid, sulfuric acid, phosphoric acid and hydrobromic acid and especially gaseous hydrogen chloride and trifluoroacetic acid. If the solvent is a strong acid, it may also be the catalyst (e.g. trifluoroacetic acid). The reaction may be carried out at a temperature from about 0° C. to 40° C., preferably from about 0° C. to 10° C. until the reaction is substantially complete. Pressure is not critical and generally the reaction is carried out at atmospheric pressure in an open system to allow the isobutylene and carbon dioxide, which are given off, to excape. This procedure for removing the N-protective group may also be used to remove those O-protective groups which may be removed by hydrolysis. The O-protective groups which may be removed by hydrolysis are $C_{1-5}$alkanoyl, benzoyl, substituted benzoyl and t-butoxycarbonyl.

Certain O-protective groups such as benzyl, substituted benzyl, diphenylmethylene, di(substituted-phenyl) methylene and di($C_{1-5}$alkyl)methylene, may be removed by hydrogenation, followed by acid treatment as described above or the acid treatment may be done first, followed by hydrogenation, or the two steps may be combined by merely adding the acidic reagent to the hydrogenation reaction mixture. The removal of these O-protective groups is accomplished by hydrogenation in a solvent with from about 10 to 50 grams of a noble metal hydrogenation catalyst per mole of ester, and preferably 30 grams per mole. The solvent may be a $C_{1-5}$alkanol, a $C_{1-5}$alkyl $C_{1-5}$alkanoate, or a mixture thereof. The noble metal hydrogenation catalysts are platinum, palladium, rhodium, ruthenium, rhenium, iridium and nickel, alone or in combination with an inert carrier such as charcoal. The reaction may be carried out at a temperature of from about 0° C. to 50° C., preferably from about 5° C. to 30° C. untill the reaction is substantially complete. The hydrogenation is usually carried out from about atmospheric to 1000 pounds per square inch gage (psig), preferably 10 to 50 psig.

The following examples are given to illustrate the invention and are not intended to limit it in any manner. All parts are given in parts by weight unless otherwise expressed. The "reduced pressure" employed in the following examples is 15 to 25 mm. Hg at 25° to 35° C. (unless otherwise indicated). When reduced pressure is employed to remove a solvent, the resultant product is oftentimes a solvate and thus the example refers to the formation of a "concentrated" product although all of the solvent has been removed with the exception of that bound in the product.

EXAMPLE 1

N-(t-Butoxycarbonyl)-3-(3,4-dihydroxyphenyl)-2-methylalanine

A mixture of 2.29 g (10.0 moles) L-3-(3,4-dihydroxyphenyl)-2-methylalanine, 2.84 g (10.0 m moles) t-butyl pentafluorophenylcarbonate, and 10 ml dimethylformamide are flushed well with nitrogen. Triethylamine (2.79 ml, 20.0 m moles) is added and the mixture stirred under nitrogen at room temperature for 24 hours. After the addition of 50 ml of water and 8 ml of 2.5 N HCl, the mixture is extracted with ethyl acetate. The extract is washed with water, saturated sodium chloride solution and dried (MgSO$_4$). Removal of the solvent in vacuum gives 2.81 g of a colorless oil.

The crude product is chromatographed on 400 g of silica gel eluting with a 70/30/3 mixture of chloroform/methanol/water. The product containing fractions are combined, the solvent removed in vacuum, and the residue dissolved in ethyl acetate and treated with dicyclohexylamine. The precipitated salt is recrystallized twice from isopropanol to give 0.31 g of L-N-(t-butoxycarbonyl)-3-(3,4-dihydroxyphenyl)-2-methylalanine cyclohexylamine salt isopropanol solvate, m.p. 148°–152° C. dec.; Calcd. for $C_{39}H_{52}N_2O_7$: C, 65.19; H, 9.48; N, 5.08; Found C, 65.24; H, 9.53; N, 4.93. The nmr and ir spectra are consistent with the assigned structure.

Similarly, when an equivalent amount of racemic 3-(3,4-dihydroxyphenyl)-2-methylalanine is used in place of the L-isomer in the above example, racemic-N-(t-butoxycarbonyl)-3-(3,4-dihydroxyphenyl)-2-methylalanine is obtained.

EXAMPLE 2

N-(t-Butoxycarbonyl)-3-(3,4-dihydroxyphenyl)-2-methylalanine

A mixture of 1.19 g (5.00 m moles) L-3-(3,4-dihydroxyphenyl)-2-methylalanine, 1.49 g (5.00 m moles) t-butyl 2,4,5-trichlorophenylcarbonate and 6 ml dimethylformamide is flushed with nitrogen and 1.39 ml (10.0 m moles) triethylamine is added. After stirring at room temperature for 24 hours, 60 ml H$_2$O and 4 ml 2.5 N HCl is added. The solution is extracted 3 times with 50 ml of ethyl acetate and the extract is washed 3 times with 50 ml of water and 1 time with 50 ml of saturated sodium chloride solution and is dried (MgSO$_4$). The solvent is removed in vacuum to give 1.98 g of a blue oil.

The crude product is dissolved in 100 ml ethyl acetate and extracted 3 times with 50 ml of 1 N aqueous sodium bicarbonate solution. This is cooled, acidified with citric acid, and the product extracted 3 times with 50 ml of ethyl acetate. After washing (2 times with 50 ml of H$_2$O nd 2 times with 50 ml of sat'd. NaCl solution) and drying (MgSO$_4$), the solvent is removed in vacuum to give 0.25 g of a colorless oil.

Similarily, when an equivalent amount of racemic-3-(3,4-dihydroxyphenyl)-2-methylalanine is used in place of the L-isomer in the above example, racemic-N-(t-butoxycarbonyl)-3-(3,4-dihydroxyphenyl)-2-methylalanine is obtained.

EXAMPLE 3

N-(1 Chloroethyl)-succinimide

N-vinylsuccinimide, 50.0 g (0.40 mole) is dissolved in 100 ml carbon tetrachloride, 5.20 g (0.020 mole) of stannic chloride is added and the mixture is stirred while saturating with hydrogen chloride gas for 6 hours at 20°-30° C. After 24 hours, the mixture is resaturated with hydrogen chloride gas for 1.5 hours. At the end of 48 hours, the solution is decanted and the gummy residue is washed with ten 100 ml portions of carbon tetrachloride. The combined extracts are slurried with 10 g of diatomaceous earth, filtered and the filtrate is concentrated under reduced pressure to approximately 400 ml. The N-(1-chloroethyl)-succinimide is filtered and dried at 20°-30° C. under reduced pressure to yield 38.4 g (59%) of white solid melting at 83.5°-84.5° C.

EXAMPLE 4

αSuccinimidoethyl N-(t-butoxycarbonyl)-3-(3,4-dihydroxyphenyl)-2-methylalaninate A mixture of 2.59 g (0.060 mole) L-N-(t-butoxycarbonyl)-3-(3,4-dihydroxyphenyl)-2-methylalanine, 9.70 g (0.060 mole) of N-(1-chloroethyl)-succinimide, 6.07 g (0.060 mole) of triethylamine and 100 ml of dry dimethylformamide is stirred at 95° for 19 hours. The reaction mixture is poured into 300 ml of water and the product extracted into three 500 ml portions of ethyl acetate. The combined organic extracts are washed with three 100 ml portions of 5% sodium bicarbonate solution, then three times with 100 ml of a saturated sodium chloride solution and dried over anhydrous magnesium sulfate. After filtering, the solution is treated with 5 g of charcoal, filtered and the solvent is evaporated under reduced pressure to give α-succinimidoethyl L-N-(t-butoxycarbonyl)-3-(3,4-dihydroxyphenyl)-2-methylalaninate as a mixture of diastereomeric isomers (α and β).

EXAMPLE 5

α-Succinimidoethyl 3-(3,4-dihydroxyphenyl)-2-methylalaninate

A suspension of 13.97 g (0.032 mole) of α-succinimidoethyl L-N-(t-butoxycarbonyl)-(3,4-dihydroxyphenyl)-2-methylalaninate in 150 ml of 25% absolute ethanol—75% ethyl acetate (by volume) solution is stirred with 8 g of anhydrous trifluoroacetic acid at 20° C. for 4 hours. The solution is filtered and the filtrate is evaporated under reduced pressure at 30° to 40° C. The residue is dissolved in 250 ml of 10% ethanol—90% ethyl acetate (by volume) solution and stirred with 20 ml of saturated sodium carbonate solution and approximately 30 g of anhydrous sodium carbonate for 10 minutes. After filtration, the filtrate is dried over anhydrous magnesium sulfate, filtered and evaporated to dryness under reduced pressure. The residue is dissolved in 130 ml of dry chloroform, the solution is cooled in an ice bath and saturated with hydrogen chloride for 15 minutes. The solid is collected, washed by suspension in 100 ml of anhydrous ether three times and then slurried in 300 ml of ethyl acetate under N₂ in a stoppered flask at room temperature overnight. The α-succinimidoethyl L-3-(3,4-dihydroxyphenyl)-2-methylalaninate hydrochloride is collected, stirred in 300 ml of hexane for 2 hours and dried in a vacuum desiccator over CaCl₂ to give the hydrochloride acid addition salt as a mixture of α and β isomers.

EXAMPLE 6

α-Chloroethylpivalate

Zinc chloride, 400 mg, is fused at 0.2–0.5 mm pressure and cooled to 25°-30° C. under nitrogen. Pivaloyl chloride, 48 g (0.40 mole), is added to the fused zinc chloride followed by acetaldehyde, 19.2 g (0.44 mole). During addition of the acetaldehyde, which is done as rapidly as possible, the reaction mixture is stirred and cooled to prevent loss of acetaldehyde due to the exothermic nature of the reaction. After heating at reflux for 1 hour, distillation gives 36 g (55%) of α-chloroethylpivalate, b.p. 32°-34° C. at 4 mm.

EXAMPLE 7

α-Pivaloyloxyethyl N-(t-butoxycarbonyl)-3-(3,4-dihydroxyphenyl)-2-methylalaninate To a stirred solution of 7.77 g (0.018 mole) of L-N-(t-butoxycarbonyl)-3-(3,4-dihydroxyphenyl-2-methylalanine in 25 ml dry dimethylformamide is added 1.80 g (0.018 mole) of triethylamine followed by 2.96 g (0.018 mole) of α-chloroethylpivalate. After stirring at 90°-95° C. for 20 hours, the reaction mixture is poured into 100 ml water and the product extracted three times with 100 ml of ethyl ether. The ether extracts are combined, washed with 50 ml of a 5% sodium bicarbonate solution. 50 ml of water and dried over anhydrous magnesium sulfate. After filtering, the solvents are removed under reduced pressure to give crude α-pivaloyloxyethyl L-N-(t butoxycarbonyl)-3-(3,4-dihydroxyphenyl)-2-methylalaninate.

EXAMPLE 8

α-Pivaloyloxyethyl L-3-(3,4-dihydroxyphenyl)-2-methylalaninate hydrochloride A solution of 8.80 g of α-pivaloyloxyethyl L-N-(t-butoxycarbonyl)-3-(3,4-dihydroxyphenyl)-2-methylalaninate in 140 ml absolute ethanol and 11 ml of an 8 N ethanolic-anhydrous hydrogen chloride solution are stirred together at 20° C. for 4 hours. The solvent and acid are removed under reduced pressure. After stirring the residue with 80 ml benzene overnight, the benzene is removed by decantation, replaced with 80 ml of hexane, stirred and the hexane decanted off. The residue is mixed with 300 ml of ethyl acetate, stirred briefly with a mixture of 5 g of solid sodium carbonate and 5 ml saturated sodium carbonate solution and dried over anhydrous magnesium sulfate. After filtering, 3 ml of 9.6 N ethanolicanhydrous hydrogen chloride is added and the solution concentrated under reduced pressure to dryness. Further drying at 65° C. and 0.2 mm pressure gives α-pivaloyloxyethyl L-3-(3,4-dihydroxyphenyl)-2-methylalaninate hydrochloride.

EXAMPLE 9

α-Succinimidoethyl L-N-(t-butoxycarbonyl)-3-(3,4-dihydroxyphenyl)-2-methylalaninate A mixture of 3.00 g (0.0096 mole) of L-N-(t-butoxycarbonyl)-3-(3,4-dihydroxyphenyl)-2-methylalanine, 1.94 g (0.012 mole) of N-(1-chloroethyl)-succinimide, 1.42 g (0.014 mole) of triethylamine and 60 ml of n-propyl acetate is stirred at reflux under nitrogen for 23.5 hours. The reaction mixture is washed with two 30 ml portions of saturated sodium bicarbonate solution and with two 40 ml portions of water and dried over anhydrous magnesium sulfate. After filtering, the solvent is evaporated under reduced pressure below 40° C. to give α-succinimidoethyl L-N-(t-butoxycarbonyl)-3-(3,4-dihydroxyphenyl)-2-methylalaninate.

EXAMPLE 10

α-Succinimidoethyl L-3-(3,4-dihydroxyphenyl)-2-methylalaninate hydrochloride

A solution of 3.50 g (0.0080 mole) of α-succinimidoethyl L-N-(t-butoxycarbonyl-3-(3,4-dihydroxyphenyl)-2-methylalaninate in 50 ml of benzene is cooled to 10° C. and saturated with hydrogen chloride for 1 hour. The mixture is evaporated under reduced pressure below 30° C. The solid residue is combined with material from a previous run (combined wt 3.51 g) and stirred for 15 minutes with a mixture of 7 ml of saturated sodium carbonate solution, 5 g of anhydrous sodium carbonate and 200 ml of 10% absolute ethanol—90% ethylacetate (by volume) solution. After filtration, the solvent is evaporated under reduced pressure below 35° C. to give 2.64 g of base. The base is dissolved in 60 ml of dry chloroform, treated with diatomaceous earth and filtered to give a clear filtrate which is saturated with hydrogen chloride for 10 minutes. The solid is collected, washed several times by suspension in anhydrous ether and dried in a vacuum desiccator to give α-succinimidoethyl L-3-(3,4-dihydroxyphenyl)-2-methylalaninate hydrochloride.

EXAMPLE 11

L-3-(3,4-Diphenylmethylenedioxyphenyl)-2-methylalanine hydrochloride

A mixture of 19.3 g (0.0777) mole of L-3-(3,4-dihydroxyphenyl)-2-methylalanine hydrochloride and 37 g (0.156 mole) of dichlorodiphenylmethane is immersed with slow stirring in a preheated oil bath at 190° C. After reaction has started, as evidenced by vigorous gas evolution, the reaction mixture is stirred rapidly for six minutes at 190° C., removed from the hot oil bath and allowed to cool to 25°–30° C. The crude product from 12 runs is combined, stirred with 3 l. of diethyl ether, filtered, washed with an additional 2 l. of diethyl ether and dried at 30° C. under 50 mm pressure. Recrystallization is accomplished by dissolving the product in ethanol and adding ethyl acetate to precipitate the product. The procedure gives 255 g (66.4%) of L-3-(3,4-diphenylmethylenedioxyphenyl)-2-methylalanine hydrochloride, m.p. 267°–268° C. dec. Anal. calcd. for $C_{23}H_{21}NO_4HCl$: C, 67.07; H, 5.39; N, 3.40. Found: C, 66.91; H, 5.29; N, 3.34.

EXAMPLE 12

L-N-(t-Butoxycarbonyl)-3-(3,4-diphenylmethylenedioxyphenyl)-2-methylalanine

A mixture of 4.12 g (10.0 m moles) of L-3-(3,4-diphenylmethylenedioxyphenyl)-2-methylalanine hydrochloride, 2.84 g (10.0 m moles) t-butyl pentafluorophenylcarbonate and 10 ml dimethylformamide is flushed well with nitrogen. Triethylamine (2.75 ml, 20.0 m moles) is added and the mixture stirred under nitrogen at room temperature for 24 hours. After the addition of 50 ml of water and 8 ml of 2.5 N HCl, the mixture is extracted with ethyl acetate. The extract is washed with water, saturated sodium chloride solution and dried (MgSO4). Removal of the solvent under reduced pressure gives L-N-(t-butoxycarbonyl)-3-(3,4-diphenylmethylenedioxyphenyl)-2-methylalanine.

EXAMPLE 13

α-Succinimidoethyl L-N-(t-butoxycarbonyl)-3-(3,4-diphenylmethylenedioxyphenyl)-2-methylalaninate A mixture of 28.5 g (0.060 mole) of L-N-(t-butoxycarbonyl)-3-(3,4-diphenylmethylenedioxyphenyl)-2-methylalanine, 9.70 g (0.060 mole) of N-(1-chloroethyl)-succinimide, 6.07 g (0.060 mole) of triethylamine and 75 ml of dry dimethylformamide is stirred at 95° C. for 19 hours. The reaction mixture is poured into 200 ml of water and the product is extracted into three 200 ml portions of ethyl acetate. The combined organic extracts are washed with three 100 ml portions of 5% sodium hydroxide solution, three 100 ml portions of saturated sodium chloride solution and dried over anhydrous magnesium sulfate. After filtering, the solution is treated with 5. g of charcoal, filtered and the solvent is evaporated under reduced pressure to give α-succinimidoethyl L-N-(t-butoxycarbonyl)-3-(3,4-diphenylmethylenedioxyphenyl)-2-methylalaninate as a mixture of diastereomeric isomers (α and β).

EXAMPLE 14

α-Succinimidoethyl L-3-(3,4-dihydroxyphenyl)-2-methylalaninate hydrochloride

A suspension of 6.0 g (0.010 mole of α-succinimidoethyl L-N-(t-butoxycarbonyl)-3-(3,4-diphenylmethylenedioxyphenyl)-2-methylalaninate in 180 ml of absolute ethanol and 9 ml of a 9.6 N ethanolic anhydrous hydrogen chloride solution is hydrogenated with 3.3 g of 10% of palladium on charcoal catalyst at an initial pressure of 30 psig until the hydrogen uptake is complete. After the removal of the catalyst by filtration, the filtrate is concentrated under reduced pressure. The residue is extracted with 50 ml of benzene and then 50 ml of ethyl acetate. The insoluble solid is then shaken with 50 ml of a 10% ethanol-90% ethyl acetate (by volume) mixture and 10 ml of a saturated sodium bicarbonate solution. After filtration, the filtrate is dried over anhydrous magnesium sulfate, filtered and concentrated under reduced pressure. The residue is redissolved in 25 ml of absolute ethanol, treated with 5 ml of 9.6 N ethanolic-anhydrous hydrogen chloride solution and concentrated under reduced pressure to give α-succinimidoethyl L-3-(3,4-dihydroxyphenyl)-2-methylalaninate hydrochloride.

What is claimed is:

1. A process for preparing the L-isomer of a compound of the formula

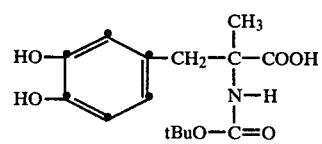

which consists essentially of treating the L-isomer of the compound having the formula with a compound of the formula
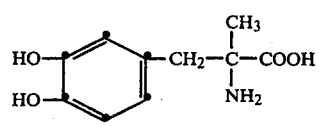
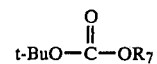
in a di-$C_{1-4}$-alkylamide solvent in the presence of triethylamine wherein $R_7$ is 2,4,5-trichlorophenyl or pentafluorophenyl.
2. The process of claim 1 wherein said di-$C_{1-4}$-alkylamide is dimethylformamide.
3. The process of claim 2 wherein $R_7$ is pentafluorophenyl.
* * * * *